US010556256B2

(12) United States Patent
Murata et al.

(10) Patent No.: US 10,556,256 B2
(45) Date of Patent: Feb. 11, 2020

(54) ANTIBACTERIAL WATER

(71) Applicant: TAKEDA PHARMACEUTICAL COMPANY LIMITED, Osaka (JP)

(72) Inventors: Naoyuki Murata, Osaka (JP); Jiichi Arai, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 356 days.

(21) Appl. No.: 15/314,187

(22) PCT Filed: May 27, 2015

(86) PCT No.: PCT/JP2015/065218
§ 371 (c)(1),
(2) Date: Nov. 28, 2016

(87) PCT Pub. No.: WO2015/182647
PCT Pub. Date: Dec. 3, 2015

(65) Prior Publication Data
US 2017/0189943 A1 Jul. 6, 2017

(30) Foreign Application Priority Data
May 28, 2014 (JP) .................................. 2014-110209

(51) Int. Cl.
| | | |
|---|---|---|
| *B82Y 30/00* | (2011.01) | |
| *B08B 3/10* | (2006.01) | |
| *A61K 47/02* | (2006.01) | |
| *A61K 47/20* | (2006.01) | |
| *A61K 33/00* | (2006.01) | |
| *C02F 1/68* | (2006.01) | |
| *A61K 47/34* | (2017.01) | |
| *A61K 47/32* | (2006.01) | |
| *A61K 9/00* | (2006.01) | |
| *A61L 2/02* | (2006.01) | |
| *A61L 9/012* | (2006.01) | |
| *C02F 1/24* | (2006.01) | |

(52) U.S. Cl.
CPC .............. *B08B 3/10* (2013.01); *A61K 9/0019* (2013.01); *A61K 33/00* (2013.01); *A61K 47/02* (2013.01); *A61K 47/20* (2013.01); *A61K 47/32* (2013.01); *A61K 47/34* (2013.01); *A61L 2/02* (2013.01); *A61L 9/012* (2013.01); *B82Y 30/00* (2013.01); *C02F 1/24* (2013.01); *C02F 1/68* (2013.01); *C02F 2303/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,143,778 A | * | 11/2000 | Gautier ................ | A61K 9/0019 514/469 |
| 2009/0011972 A1 | | 1/2009 | Suzuki et al. | |
| 2010/0151043 A1 | | 6/2010 | Mano et al. | |
| 2010/0310665 A1 | * | 12/2010 | Watson ................ | A61K 31/137 424/489 |
| 2012/0128749 A1 | | 5/2012 | Tsuji et al. | |
| 2015/0010604 A1 | * | 1/2015 | Ishii ....................... | A01N 25/34 424/405 |
| 2015/0250728 A1 | * | 9/2015 | Murata ................... | A61K 9/14 560/18 |

FOREIGN PATENT DOCUMENTS

| | | |
|---|---|---|
| JP | 2006-206896 | 8/2006 |
| JP | 2013-180956 | 9/2013 |
| WO | 91/15244 | 10/1991 |
| WO | 2008/072371 | 6/2008 |
| WO | 2011/016529 | 2/2011 |
| WO | 2014/050910 | 4/2014 |

OTHER PUBLICATIONS

Cho et al., title: Ultrasonic formation of nanobubbles and their zeta-potentials in aqueous electrolyte and surfactant solutions; Colloids and Surfaces A: Physicochem. Eng. Aspects, vol. 269, pp. 28-34, available online Aug. 16, 2005 (Year: 2005).*
Hirai et al, title: Development of high density micro-bubble generator for environmental technology, Electronics and Electrical Engineering, vol. 92. Issue 4, p. 37-40, 2009. (Year: 2009).*
Alkhalidi et al, title: Factor Affecting Bubble Creation and Bubble Size; IMECE2011-6211; Proceedings of the ASME 2011 International Mechanical Engineering Congress & Exposition; dated Nov. 11-17, 2011. (Year: 2011).*
Extended European Search Report dated Jan. 23, 2018 in European Application No. 15799779.2.

(Continued)

*Primary Examiner* — Yanzhi Zhang
(74) *Attorney, Agent, or Firm* — Wenderoth, Lind & Ponack, L.L.P.

(57) ABSTRACT

A novel technique is provided for preserving a liquid pharmaceutical preparation safely and stably. The nano-bubble water of the present invention, which is produced in the presence of a surfactant, a hydrophilic resin and/or an electrolyte and contains not less than $2.0 \times 10^8$ bubbles/mL of nano-bubbles, shows a superior antibacterial action, and can be used as a base of a liquid pharmaceutical preparation showing safe and stable preservation property.

6 Claims, 1 Drawing Sheet

(56) References Cited

OTHER PUBLICATIONS

Cho et al., "Ultrasonic formation of nanobubbles and their zeta-potentials in aqueous electrolyte and surfactant solutions", Colloids and Surfaces A: Physicochem. Eng. Aspects, 269; 28-34 (2005).
International Search Report dated Jul. 28, 2015 in corresponding International Application No. PCT/JP2015/065218.
Shigeo et al., "The high-concentrated stable production of ID 100 nm—nano-bubbles by nanoGALF technology", The Japanese Society for Multiphase Flow, Lecture Meeting, 2011, pp. 1-2.

* cited by examiner

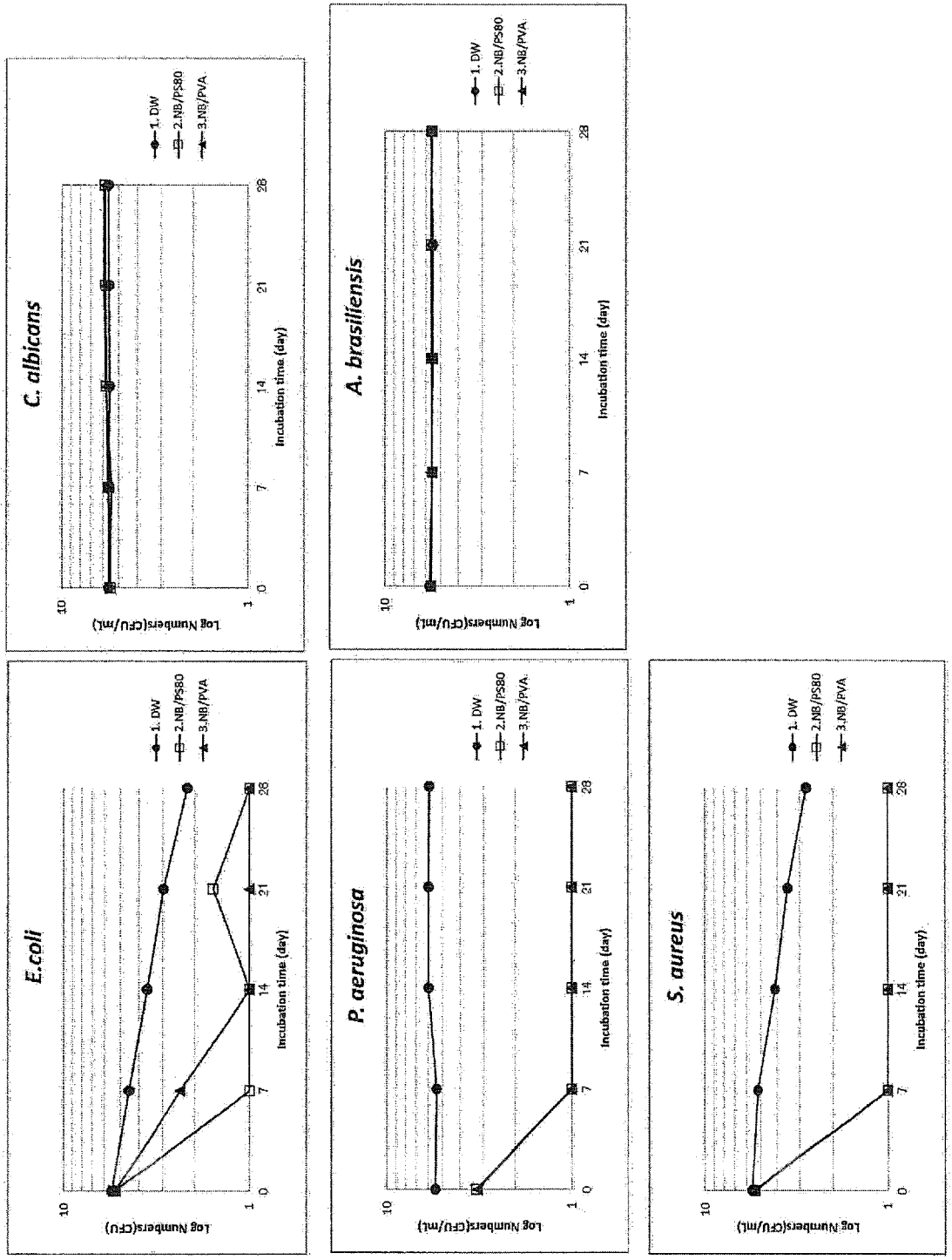

ANTIBACTERIAL WATER

TECHNICAL FIELD

The present invention relates to high density nano-bubble water, a production method of high density nano-bubble water, a method of maintaining high density nano-bubbles for a long term, and nano-bubble water having an antibacterial action. More particularly, it relates to nano-bubble water having an antibacterial action enhanced by an increase in the number of nano-bubbles, and a method of increasing the number of nano-bubbles in nano-bubble water and the like.

BACKGROUND OF THE INVENTION

Nano-bubble water is currently used for a washing step of semiconductors and for the promotion of the growth of crops. Heretofore, nano-bubbles could be formed only at a low density, it was difficult to maintain presence of nano-bubbles in water for a long time and maintain the effect thereof. Therefore, utilization of nano-bubble water has been limited to use requiring presence of nano-bubbles for a short time such as cleansing of tools and the like.

Injections such as vaccine preparation and the like are largely divided into 2 kinds of single administration type and multiple administration type.

In a single administration type injection, only a single dosage of a drug solution such as a sterilization treated vaccine solution and the like is tightly sealed in an individual vial to prevent bacterial contamination. Since a single administration type injection uses the entire drug solution at one time, addition of a preservative does not need to be considered. However, since the production cost of such single administration type injection is high, use thereof particularly in the developing countries (e.g., prophylactic inoculation of vaccine preparation etc.) is not realistic.

On the other hand, in a multiple administration type injection containing a drug solution such as a vaccine and the like in an amount for several people in one vial, a preservative such as thimerosal, phenoxyethanol, para-hydroxybenzoate, phenol and the like is contained in the drug solution, as a preservative for killing or suppressing growth of bacterium that was mixed during puncture of the injection needle, since it is punctured multiple times through the rubber closure portion of the vial when in use.

Patent document 1 describes that a composition containing ultrafine bubbles and a medicament expresses the effect of the medicament more, and when a medicament is dispersed in aqueous ultrafine bubble solution, a stable dispersion can be obtained without using a surfactant. Example 1 describes ultrafine bubble water at $4.0$-$8.0 \times 10^6$ bubbles/mL. FIG. 4 describes that ultrafine bubbles are stably present for 300 hr. However, ultrafine bubble water containing ultrafine bubbles at not less than $2.0 \times 10^8$ bubbles/mL and an antibacterial action of the ultrafine bubble water are not described.

Non-patent document 1 describes that nano-bubble water was produced using a nano-bubble generating apparatus (nanoGALF™) and under the conditions of distilled water 4.0 L, bubble water flow rate 4.0 L/min, dissolution pressure 0.3 MPa, 30 min, and the number of nano-bubbles was measured using LM20 (NanoSight) to obtain nano-bubble water with $1.42 \times 10^8$ bubbles/mL. However, nano-bubble water comprising not less than $2.0 \times 10^8$ bubbles/mL of nano-bubbles and an antibacterial action of the nano-bubble water itself are not described. It also describes that the nano-bubble water stably maintains nano-bubbles at $1.0 \times 10^8$ bubbles/mL in water for about 3 days immediately after production, but nano-bubbles disappear when the number of the nano-bubbles is measured after 4 months of storage.

DOCUMENT LIST

Patent Document patent document 1: WO 2011/016529

Non-Patent Document non-patent document 1: The Japanese Society for Multiphase. Flow lecture meeting 2011, "High density, stable production of nano-bubble with diameter 100 nm by nanoGALF technique"

SUMMARY OF THE INVENTION

Problems to be Solved by the Invention

Thimerosal used as a preservative for liquid pharmaceutical preparations such as vaccine preparation and the like is an ethyl mercury compound feared for potential toxicity, and the development of a technique that shows a preservation effect without using thimerosal, and stably preserves a liquid pharmaceutical preparation such as vaccine preparation and the like has been desired. Therefore, an object of the present invention is to provide a technique for stably preserving a liquid pharmaceutical preparation (e.g., injection) without using a preservative feared for potential side effects such as thimerosal.

Another object of the present invention is to provide, in an attempt to expand use and application field of the nano-bubble water, higher density nano-bubble water than nano-bubble water obtained by conventional production techniques.

A still another object of the present invention is to provide, in an attempt to maintain the effect of nano-bubble water for a long term, a method of maintaining high density nano-bubble for a long term.

Means of Solving the Problems

In view of the above-mentioned problems, the present inventors have conducted intensive studies and found that the number of nano-bubbles strikingly increases, i.e., high density nano-bubbles are produced, by adding a surfactant, a hydrophilic resin, an electrolyte and the like during preparation of nano-bubble water. In addition, they have found that the number of nano-bubbles of nano-bubble water prepared in the presence of a surfactant, a hydrophilic resin, an electrolyte and the like is maintained for a long term. In addition, they have found that nano-bubble water prepared in the presence of a surfactant, a hydrophilic resin, an electrolyte and the like shows preservative effectiveness meeting the standard of a preservative in the Preservatives-Effectiveness Tests by reference to the United States Pharmacopoeia (USP), and is sufficiently usable as a base of a liquid pharmaceutical preparation (e.g., injection). That is, they have found that conventional preservatives such as thimerosal, phenoxyethanol, para-hydroxybenzoate, phenol and the like do not need to be added or the amount thereof to be added can be made extremely small by using the nano-bubble water having an increased number of nanobubbles of the present invention as a base of a liquid pharmaceutical preparation, which resulted in the completion of the present invention.

That is, the present invention relates to

[1] nano-bubble water comprising not less than $2.0 \times 10^8$ bubbles/mL of nano-bubbles;
[2] the nano-bubble water of the above-mentioned [1], which has an antibacterial action;
[3] the nano-bubble water of the above-mentioned [1], which is produced in the presence of a surfactant, a hydrophilic resin and/or an electrolyte;
[4] the nano-bubble water of the above-mentioned [1], which is produced in the presence of polysorbate 80 and/or poly(vinyl alcohol);
[5] a method of increasing the number of nano-bubbles in nano-bubble water to not less than $2.0 \times 10^8$ bubbles/mL, comprising producing the nano-bubble water in the presence of a surfactant, a hydrophilic resin and/or an electrolyte;
[6] the method of the above-mentioned [5], wherein the nano-bubble water is produced in the presence of polysorbate 80 and/or poly(vinyl alcohol);
[7] a method of maintaining the number of nano-bubbles in nano-bubble water at not less than $2.0 \times 10^8$ bubbles/mL, comprising producing the nano-bubble water in the presence of a surfactant, a hydrophilic resin and/or an electrolyte;
[8] the method of the above-mentioned [7], wherein the nano-bubble water is produced in the presence of polysorbate 80 and/or poly(vinyl alcohol);
[9] the method of the above-mentioned [8], wherein the number of nano-bubbles in the nano-bubble water is maintained at not less than $2.0 \times 10^8$ bubbles/mL for not less than 3 months;
[10] a method of potentiating an antibacterial action of nano-bubble water, comprising setting the number of nano-bubbles contained in the nano-bubble water to not less than $2.0 \times 10^8$ bubbles/mL;
and the like.

Effect of the Invention

The nano-bubble water containing an increased number of nano-bubbles, i.e., high density nano-bubble water, of the present invention shows a superior antibacterial action and preservative effectiveness afforded thereby, and is useful as a base of a multiple administration type liquid pharmaceutical preparation (e.g., injection), which is repeatedly used from the same container for a given period. When the nano-bubble water having an increased number of nano-bubbles of the present invention is used as a base of a liquid pharmaceutical preparation, since an inorganic or organic compound does not need to be contained separately as a preservative, the concern about side effects is less, and high density nano-bubbles are maintained for a long term, a preparation permitting stable preservation can be provided, which is extremely useful.

In the nano-bubble water containing an increased number of nano-bubbles, i.e., high density nano-bubble water, of the present invention, various effects provided by nano-bubble water itself are enhanced, and therefore, utilization and development in various fields such as enhancement of detergency and the like are expected.

In addition, since a method of maintaining high density nano-bubbles of the present invention for a long term is provided, the action of nano-bubble water can be maintained for a long term, and therefore, utilization and development in various fields such as enhancement of growth of crops, enhancement of detergency performance of precision instrument, enhancement of soil cleaning and the like are expected.

BRIEF DESCRIPTION OF THE DRAWINGS

FIG. 1 is a graph showing the results of the Preservatives-Effectiveness Tests of nano-bubble water produced in the presence of particular additives. In FIG. 1, -●- shows the results of water for injection, -□- shows the results of nano-bubble water containing polysorbate 80, and -▲- shows the results of nano-bubble water containing poly(vinyl alcohol).

DETAILED DESCRIPTION OF THE INVENTION

The nano-bubble water of the present invention characteristically contains not less than $2.0 \times 10^8$ bubbles/mL of nano-bubbles.

In the present specification, "nano-bubble water" means water in which gas particles (nano-bubbles) having a diameter of not more than 1000 nm are stably present. The diameter of nano-bubbles (nano-bubble diameter) is preferably not more than 800 nm, more preferably not more than 500 nm. While the lower limit of the nano-bubble diameter is not particularly limited, it is, for example, not less than 1 nm, preferably not less than 5 nm, more preferably not less than 10 nm. The average diameter of the nano-bubble can be appropriately determined within the range of not more than 500 nm, preferably 1-500 nm, and appropriately determined within the range of preferably 5-300 nm, more preferably 10-150 nm. In the present specification, the average diameter means a particle size (mode diameter) corresponding to the most frequent value (maximum value of % by volume or % by number) of distribution.

The size of the nano-bubble is desirably uniform, and d90/d10 ratio wherein d10 is a nano-bubble diameter corresponding to the accumulative 10% from the small diameter side and d90 is a nano-bubble diameter corresponding to the accumulative 90% from the small diameter side of the nano-bubble diameter distribution is preferably not more than 5, more preferably not more than 4.5.

The number of nano-bubbles contained in the nano-bubble water of the present invention means the number of nano-bubbles present in 1 mL of nano-bubble water. In the present specification, it is sometimes to be referred to as "nano-bubble density".

The nano-bubble water of the present invention is characterized in that the number of nano-bubbles contained therein is not less than $2.0 \times 10^8$ bubbles/mL, by which a superior action effect (e.g., antibacterial action, preservative effectiveness, detergency, crop growth promoting action) is provided.

From the aspects of action effect such as antibacterial action, preservative effectiveness and the like, the number of nano-bubbles is preferably not less than $2.0 \times 10^8$ bubbles/mL, more preferably not less than $2.5 \times 10^8$ bubbles/mL.

While the upper limit of the number of nano-bubbles is not particularly limited, it may be not more than $2.0 \times 10^9$ bubbles/mL, preferably not more than $1.0 \times 10^9$ bubbles/mL.

The nano-bubble diameter, distribution thereof, and the number of nano-bubbles can be measured by a method utilizing scattering of laser beam based on the Brownian motion (e.g., NanoSight, LM20, LM10 and the like), a method based on impedance changes (e.g., Beckman Coulter, Multisizer4 and the like), a method based on the laser diffraction scattering method (e.g., Shimadzu Corporation, SALD-7100H and the like), a method utilizing Mie scattering (e.g., NIPPON DENSHOKU INDUSTRIES Co., LTD, NP-500T and the like) and the like. As the nano-bubble diameter and distribution thereof of nano-bubble water or aqueous nano-bubble solution to be used in the present invention, those measured by a tracking method (tracking method) utilizing laser beam scattering using LM20 and LM10, NanoSight, or those measured according thereto are used.

While the values of nano-bubble diameter, distribution thereof, and the number of nano-bubbles generally mean those measured immediately after production of nano-bubble water, they may be values of nano-bubble diameter, distribution thereof, and the number of nano-bubbles which are measured immediately before use after airtight storage for a given period (e.g., about 6 months) after production of the nano-bubble water, since the nano-bubble diameter, distribution thereof and the number of nano-bubbles of the nano-bubble water of the present invention are stably maintained for a long term as mentioned below.

Examples of the gas constituting nano-bubbles include, but are not limited to, oxygen, ozone, nitrogen, carbon dioxide, helium, argon and the like, or a mixture of one or more gases selected from oxygen, ozone, nitrogen, carbon dioxide, helium, argon and the like, gas in air (e.g., air) and the like. Preferred are nitrogen, ozone, oxygen and argon, and more preferred are nitrogen and ozone. Alternatively, the inside of the nano-bubble may be a vacuum.

The "vacuum" here means the state of a gap filled with a gas at a lower pressure than the general atmosphere.

On the other hand, the "water" containing nano-bubbles is not particularly limited and, for example, tap water, deionized water, distilled water, sterile distilled water, purified water for injection, ultrapure water and the like can be used. When used for injection, sterile distilled water, purified water for injection and the like are preferable.

As the "aqueous solution" in the present specification, for example, water further containing any additive generally used in the field of drug formulation can be mentioned. Examples of such additive include excipient, lubricant, binder, disintegrant, solubilizing agent, suspending agent, isotonicity agent, buffering agent, soothing agent, preservative, antioxidant, colorant, sweetening agent, pH adjuster, stabilizer, acidulant, flavor, fluidizer and the like. Preferable examples are those similar to the pharmacologically acceptable carriers mentioned below.

Two or more kinds of the above-mentioned additives may be used as a mixture at an appropriately ratio. As the additive, one or more additives selected from suspending agent, stabilizer, dispersing agent, isotonicity agent and the like can be preferably mentioned.

The "aqueous nano-bubble solution" in the present specification is, for example, nano-bubble water further containing any additive generally used in the field of drug formulation. Examples of such additive include excipient, lubricant, binder, disintegrant, solubilizing agents, suspending agent, isotonicity agent, buffering agent, soothing agent, preservative, antioxidant, colorant, sweetening agent, pH adjuster, stabilizer, acidulant, flavor, fluidizer and the like.

Two or more kinds of the above-mentioned additives may be used as a mixture at an appropriate ratio. As the additive, one or more additives selected from suspending agent, stabilizer, dispersing agent, isotonicity agent and the like can be preferably mentioned.

These additives may be, as long as they do not influence the production and/or stability of nano-bubbles, dissolved in advance in water and directly prepared as an aqueous nano-bubble solution. Alternatively, nano-bubbles may be generated in water without containing an additive to give nano-bubble water and additive may be dissolved when in use to give an aqueous nano-bubble solution.

As a production method of nano-bubble water, a method including simultaneously generating micro-bubbles (gas particles having diameter of about 1-60 μm) and nano-bubbles in water, separating micro-bubbles by floating them to leave only the nano-bubbles, and a method including direct generation of nano-bubbles are used largely, and the former is the mainstream method at present. The former method includes a high-speed swirl water flow type wherein a gas is disrupted by high-speed swirl to generate many micro-bubbles, micro-bubbles are separated by floating them to leave only the nano-bubbles in water, a pressurization dissolution type wherein a gas is pressurized and dissolved in a supersaturation state and the resulting solution is rapidly depressurized to generate micro-bubbles and nano-bubbles, the micro-bubbles are separated by floating to leave nano-bubbles in water and the like.

A production method of the nano-bubble water of the present invention is preferably a pressurization dissolution type. For example, a gas is forcedly dissolved in a pressurization container pressurized to about 0.2-0.5 MPa by a pressurization pump, and flashed out into water through a nozzle, whereby the gas supersaturated by depressurization is released as micro-bubbles or nano-bubbles in the discharged water to provide a clouded mixture of micro-bubble water and nano-bubble water. Thereafter, aeration is discontinued and the mixture is stood to allow for natural floating and release of the micro-bubbles, whereby clear nano-bubble water containing only nano-bubbles is produced. Therefore, the pressurization dissolution type is different from other type wherein a gas absorbed in a working fluid directly generates gas bubbles, on the point that gas bubbles are secondarily generated via a two-step process of generation by pressurization dissolution-depressurization.

Examples of the nano-bubble generation apparatus include pressurization dissolution type (nanoGALF™ manufactured by IDEC, OM4-MD5-045 manufactured by AURA TEC CO., LTD., micro-bubble generator manufactured by Nikuni Corporation and the like), and high-speed swirl water flow type (YJ manufactured by bi-clean, micro-bubble generation apparatus manufactured by AQUAAIE, Microblade manufactured by ROYAL ELECTRIC CO., LTD. and the like). The nano-bubble generation apparatus is preferably pressurization dissolution type nanoGALF™ manufactured by IDEC.

In the present specification, "to increase the number of nano-bubbles" means to increase the number of nano-bubbles in nano-bubble water by producing nano-bubble water in the presence of particular additives, as compared to those in the absence of the additives. In the nano-bubble water of the present invention, the number of nano-bubbles can be increased by subjecting "water" or "aqueous solution" to the above-mentioned production method of nano-bubble water in the presence of a surfactant, a hydrophilic resin and/or an electrolyte.

For example, in nano-bubble water produced in the present invention in the presence of a surfactant, a hydrophilic resin and/or an electrolyte, the number of nano-bubbles can be increased as compared to nano-bubble water prepared from water without containing a surfactant, a hydrophilic resin and an electrolyte. In addition, nano-bubble water produced in the present invention in the presence of a surfactant, a hydrophilic resin and/or an electrolyte shows a superior antibacterial action as compared to nano-bubble water prepared from water without containing a surfactant, a hydrophilic resin or an electrolyte.

The surfactant, hydrophilic resin and electrolyte may be used alone, or two or more thereof may be used in combination.

Examples of the surfactant to be used in the present invention include anionic surfactant (sodium lauryl sulfate and the like), non-ionic surfactant [glycerin fatty acid ester such as glyceryl monostearate and the like, sucrose ester of fatty acid, sorbitan ester of fatty acid such as sorbitan monostearate, sorbitan monolaurate and the like, polyglyceryl fatty acid ester, polyoxyethylene(hydrogenated) castor oil, polyoxyethylene sorbitan fatty acid ester (polyoxyethylene sorbitan lauric acid ester (polysorbate 20 and the like), polyoxyethylene sorbitan oleic acid ester (polysorbate 80 and the like) and the like), polyethylene glycol fatty acid ester, polyoxyethylene alkyl ether (polyoxyethylene lauryl ether and the like), polyoxyethylene polyoxypropylene alkyl ether (polyoxyethylene polyoxypropylene cetyl ether and the like), polyoxyethylene alkyl phenyl ether (polyoxyethylene nonyl phenyl ether and the like), macrogols, polyoxyethylene polyoxypropylene glycol (poloxamer 407, poloxamer 235, poloxamer 188, poloxamine and the like) and the like], cationic surfactant (e.g., benzalkonium chloride, benzethonium chloride, cetyl pyridinium chloride, hexadecyltrimethylammonium bromide, dequalinium chloride etc.), amphoteric surfactant (e.g., cocamide propyl betaine, cocamide propyl hydroxy sultaine etc.). Sodium lauryl sulfate, polysorbate 80 and the like are preferable, and polysorbate 80 is more preferable. The above-mentioned surfactant may be used alone, or two or more thereof may be used in combination.

Examples of the hydrophilic resin to be used in the present invention include acrylic resins such as polyacrylamide, polyacrylic acid or alkali metal salt thereof, an ester thereof and the like, vinyl resin such as polyvinylpyrrolidone, poly(vinyl alcohol), poly(vinyl ethyl ether) and copolymer thereof and the like, natural polysaccharides such as gum tragacanth, caraya gum and the like, methylcellulose, hydroxypropylcellulose, hydroxypropylmethylcellulose, hyaluronic acid, alkali metal salt thereof, agarose, curdlan and the like. Poly(vinyl alcohol), hydroxypropylcellulose and the like are preferable, and poly(vinyl alcohol) is more preferable. The above-mentioned hydrophilic resins may be used alone, or two or more thereof may be used in combination.

Examples of the electrolyte to be used in the present invention include sodium salt such as sodium chloride, sodium bromide, sodium iodide, sodium fluoride, sodium hydrogen carbonate, sodium carbonate, sodium percarbonate, sodium sulfite, sodium sulfate, sodium thiosulfate and the like, calcium salt such as calcium chloride, calcium sulfate and the like, magnesium salt such as magnesium chloride, magnesium sulfate, magnesium oxide, magnesium peroxide, magnesium carbonate and the like, and the like, and sodium chloride, calcium chloride, sodium carbonate and the like are preferable. The above-mentioned electrolytes may be used alone, or two or more thereof may be used in combination.

As the surfactant, hydrophilic resin and/or electrolyte to be used in the present invention, a surfactant (e.g., polysorbate 80) and/or a hydrophilic resin (e.g., poly(vinyl alcohol)) are/is preferable.

While the contents of the surfactant, hydrophilic resin and/or electrolyte to be used in the present invention in water are not particularly limited as long as they can be used for a desired use (e.g., liquid pharmaceutical preparation such as injection and the like), the upper limits thereof are preferably not more than 50% (W/V), more preferably not more than 20% (W/V), further preferably not more than 10% (W/V). While the lower limits are not particularly limited as long as they can be used for a desired use (e.g., liquid pharmaceutical preparation such as injection and the like), it is preferably not less than 0.01% (W/V), more preferably not less than 0.05% (W/V), further preferably not less than 0.1% (W/V), from the aspect of the effect to increase the number of nano-bubbles. As used herein, (W/V) means g/mL.

When two or more of the surfactant, hydrophilic resin and electrolyte are used in combination, the total amount thereof is the content in water.

One embodiment of the present invention is a method of maintaining the number of nano-bubbles in nano-bubble water at not less than $2.0 \times 10^8$ bubbles/mL, which comprises producing nano-bubble water in the presence of a surfactant, a hydrophilic resin and/or an electrolyte.

In this embodiment, the contents of the surfactant, hydrophilic resin and/or electrolyte are similar to those of the above-mentioned surfactant, hydrophilic resin and/or electrolyte in nano-bubble water.

To "maintain the number of nano-bubbles at not less than $2.0 \times 10^8$ bubbles/mL" means that nano-bubbles maintaining the above-mentioned number of nano-bubbles are present in water for the period when, for example, the action effect (e.g., antibacterial action, detergency, crop growth promoting action etc.) of the nano-bubble water of the present invention is required to be maintained (e.g., when used as base for injection, the effective period thereof).

In the nano-bubble water of the present invention, the number of nano-bubbles of not less than $2.0 \times 10^8$ bubbles/mL, at which a superior antibacterial action is provided, can be maintained for a long term. Specifically, the number of nano-bubbles of not less than $2.0 \times 10^8$ bubbles/mL can be maintained for preferably not less than 3 months, more preferably not less than 6 months, further preferably not less than one year and, for example, an antibacterial action can be maintained for the effective period of general injections. While the upper limit of the period during which the number of nano-bubbles of not less than $2.0 \times 10^8$ bubbles/mL is to be maintained is not particularly limited, it is preferably not more than 5 years, more preferably not more than 3 years, further preferably not more than 1 year.

In the present specification, to "have an antibacterial action" means to show an antibacterial action of the level satisfying the standard of the Preservatives-Effectiveness Tests according to, for example, the Japanese Pharmacopoeia (JP), United States Pharmacopeia (USP), British Pharmacopoeia (B.P.), European Pharmacopoeia (EP) and the like.

In the present specification, to "potentiate an antibacterial action of nano-bubble water" means that the preservative effectiveness to be measured by the above-mentioned test is enhanced by containing not less than $2.0 \times 10^8$ bubbles/mL of nano-bubbles.

Examples of the specific bacteria, on which the nano-bubble water of the present invention shows an antibacterial action, include bacterium of the genus *Staphylococcus* such as *Staphylococcus aureus* and the like; bacterium of the genus *Streptococcus* such as *Streptococcus pyogenes, Streptococcus* spp., *Streptococcus agalactiae, Streptococcus bovis, Streptococcus pneumoniae, Streptococcus mutans* and the like; *Enterococcus* spp.; bacterium of the genus *Neisseria* such as *Neisseria gonorrhoeae, Neisseria meningitides* and the like; bacterium of the genus *Bacillus* such as Bacillus anthracis, Bacillus subtilis and the like; bacterium of the genus Propionibacterium such as Propionibacterium acnes and the like; bacterium of the genus Corynebacterium such as Corynebacterium diphtheriae and the like; bacterium of the genus Listeria such as Listeria monocytogenes and the like; bacterium of the genus Clostridium such as Clostridium tetani, Clostridium difficile and the like; bacterium of the genus Escherichia such as Escherichia coli and the like; Enterobacter spp.; bacterium of the genus Pseudomonas such as Pseudomonas aeruginosa and the like; bacterium of the genus Klebsiella such as Klebsiella pneumoniae and the like; bacterium of the genus Salmonella (Salmonella spp.); bacterium of the genus Shigella (Shigella spp.) and the like.

Examples of the specific fungi, on which the nano-bubble water of the present invention shows an antibacterial action, include various filamentous fungi (e.g., fungi of the genus Microsporum such as Microsporum canis, Microsporum audouinii, Microsporum gypseum and the like; fungi of the genus Trichophyton such as Trichophyton rubrum, Trichophyton mentagrophytes, Trichophyton Trichophyton, Trichophyton schoenleinii, Trichophyton tonsurans and the like; fungi of the genus Acremonium (Acremonium spp.); fungi of the genus Fusarium such as Fusarium oxysporum and the like; fungi of the genus Scopulariopsis such as Scopulariopsis brevicaulis and the like; fungi of the genus Scytalidium such as Scytalidium dimidiatum and the like), various yeasts (e.g., fungi of the genus Candida such as Candida albicans, Candida tropicalis and the like; fungi of the genus Saccharomyces such as Saccharomyces cerevisiae and the like; fungi of the genus Malassezia such as Malassezia furfur and the like; fungi of the genus Cryptococcus such as Cryptococcus neoformans and the like; fungi of the genus Aspergillus such as Aspergillus fumigatus, Aspergillus nidulans, Aspergillus niger, Aspergillus brasiliensis and the like; fungi of the genus Coccidioides such as Coccidioides immitis and the like) and the like.

Of these, the nano-bubble water is superior in the antibacterial action on, in bacteria, bacterium of the genus Escherichia, bacterium of the genus Staphylococcus, and bacterium of the genus Pseudomonas, and effectively suppresses growth of particularly Escherichia coli, Pseudomonas aeruginosa and/or Staphylococcus aureus. Also, the nano-bubble water is superior in the antibacterial action on, in fungi, fungi of the genus Candida and fungi of the genus Aspergillus, and effectively suppresses growth of particularly Candida albicans and/or Aspergillus brasiliensis.

The nano-bubble water of the present invention shows a superior antibacterial action and preservative effectiveness afforded thereby, and is useful as a base of a multiple administration type liquid pharmaceutical preparation which is repeatedly used for a given period from the same container, such as injection (e.g., subcutaneous injection, intravenous injection, intramuscular injection, intraperitoneal injection, drip infusion, intracerebral administration injection, intracerebrospinal fluid administration injection, intraocular administration injection), eye drop, syrup, liquid, emulsion, suspension and the like. Furthermore, the nano-bubble water of the present invention can also be preferably used as a base of a liquid product which is repeatedly used for a given period from the same container, such as cosmetics (e.g., skin lotion, toner, tonic etc.) and food (e.g., drinks etc.).

In addition, for example, nano-bubble water preserved for a given period after preparation can be preferably used for applications such as tool cleaning, crop growth promotion and the like, for which nano-bubble water prepared when in use is conventionally used.

When the nano-bubble water of the present invention is used as a base of a liquid pharmaceutical preparation, the pharmaceutically active ingredient is not particularly limited, and examples thereof include various vaccines (e.g., influenza vaccine, rubella vaccine, Japanese encephalitis vaccine etc.), peptide compound having a physiological activity, antibiotic, antifungal drug, antihyperlipidemic drug, antitumor drug, antipyretic drug, analgesic drug, antiphlogistic drug, antitussive-expectorant drug, sedating drug, muscle relaxant drug, antiepileptic drug, antiulcer drug, antidepressant drug, antiallergic drug, cardiotonic drug, antiarrhythmic drug, vasodilatory drug, hypotensive-diuretic drug, therapeutic drug for diabetes, anticoagulant, hemostatic, anti-platelet drug, antiphthisic drug, hormone drug, antinarcotic drug, osteoclastic inhibitor, osteogenesis-promotion enhancer, angiogenesis inhibitor and the like. Particularly, it can be preferably used for various vaccines such as influenza vaccine and the like, for which thimerosal is used as a preservative.

When the nano-bubble water of the present invention is used as a base of a liquid pharmaceutical preparation, it can be formulated as a liquid pharmaceutical preparation by a conventional method in the field of drug formulation, and administered to mammals (e.g., human, mouse, rat, rabbit, dog, cat, bovine, horse, swine, monkey) for the prophylaxis or treatment of various diseases.

To be specific, the above-mentioned pharmaceutically active ingredient is added to the nano-bubble water of the present invention, and gently mixed to give an aqueous solution or suspension.

The above-mentioned aqueous solution and suspension can contain a pharmaceutically acceptable carrier in an amount acceptable to human or animal.

As the pharmaceutically acceptable carrier, a pH regulator such as monosodium phosphate, dipotassium phosphate, disodium phosphate, monopotassium phosphate, sodium hydroxide, hydrochloric acid and the like, an antibiotic such as kanamycin sulfate, erythromycin lactobionate, penicillin G potassium and the like, a stabilizer such as lactose, potassium glutamate, D-sorbitol, aminoacetic acid, human serum albumin and the like, a colorant such as phenol red and the like, an isotonicity agent such as sodium chloride, potassium chloride and the like, and the like can be added.

The aqueous solution and suspension are tightly sealed in a vial or ampoule and preserved. Preservation is preferably performed under shading conditions.

The preservation temperature is preferably not more than room temperature, more preferably not more than 10° C.

EXAMPLES

The present invention is explained in more detail in the following by referring to Examples, which are not to be construed as limitative in any manner.

Example 1: Increasing Effect on the Number of Nano-Bubbles by Additive

An increasing effect on the number of nano-bubbles when polysorbate 80, poly(vinyl alcohol) (PVA), sodium lauryl sulfate or NaCl was used as additive was measured.

Each additive (2 g) was dissolved in water for injection (2 L), and nano-bubble water was prepared using nano-bubble generating apparatus (nanoGALF™FZ1N-02) manufactured by IDEC and under the following setting.
  bubble water flow about 4.0 L/min
  dissolution pressure 300 KPa±5%

As a control, nano-bubble water was similarly prepared from water for injection (2 L) alone.

The number of nano-bubbles in the prepared nano-bubble water was measured by a tracking method utilizing laser beam scattering using LM20 or LM10 by NanoSight.

The results are shown in Table 1.

TABLE 1

| additive | number of nano-bubbles (bubbles/mL) | control ratio |
| --- | --- | --- |
| no additive (control) | $0.62 \times 10^8$ | — |
| polysorbate 80 | $4.05 \times 10^8$ | about 7-fold |
| poly(vinyl alcohol) | $3.94 \times 10^8$ | about 6.5-fold |
| sodium lauryl sulfate | $2.82 \times 10^8$ | about 4.5-fold |
| NaCl | $2.57 \times 10^8$ | about 4-fold |

It was clarified that addition of a surfactant, a hydrophilic resin or an electrolyte strikingly increased the number of nano-bubbles, and nano-bubble water containing nano-bubbles at not less than $2.0 \times 10^8$ bubbles/mL can be produced stably.

Example 2: Preservative Effectiveness of Nano-Bubble Water

Using a method according to the Preservatives-Effectiveness Tests described in United States Pharmacopoeia (USP <51> "Antimicrobial effectiveness testing"), the preservative effectiveness of nano-bubble water produced in Example 1 was evaluated.

Each of *Escherichia coli*, *Pseudomonas aeruginosa*, *Staphylococcus aureus* was mixed with nano-bubble water, and preserved at 20-25° C. On days 0, 7, 14, 28, viable counts were measured using the test conditions and test method described in United States Pharmacopoeia (USP <51> "Antimicrobial effectiveness testing").

Each of *Candida albicans* and *Aspergillus brasiliensis* was mixed with nano-bubble water and preserved at 20-25° C. For the Preservatives-Effectiveness Tests of these fungi, the same liquid culture medium as in the Preservatives-Effectiveness Tests of the above-mentioned *Escherichia coli*, *Pseudomonas aeruginosa* and *Staphylococcus aureus* was used, rather than the culture medium (sabouraud glucose medium or sabouraud glucose agar medium) described in United States Pharmacopoeia (USP <51> "Antimicrobial effectiveness testing"). As for other test conditions and test method, viable counts were measured according to the United States Pharmacopoeia (USP <51> "Antimicrobial effectiveness testing"). An antibacterial effect was evaluated to be present when the fungi did not grow from the start of the test (day 0).

The results are shown in FIG. 1.

The nano-bubble water of the present invention containing nano-bubble at not less than $2.0 \times 10^8$ bubbles/mL showed an antibacterial action on all of these 5 kinds of bacteria and fungi, which meets the standard of a preservative according to the United States Pharmacopoeia (USP).

Example 3: Nano-Bubble Number Maintaining Effect of Additive

Using polysorbate 80 or poly(vinyl alcohol) as an additive, nano-bubble water prepared according to the method of Example 1 was preserved under the conditions of 25° C., 60% RH for 6 months or 12 months. The number of nano-bubbles contained in the nano-bubble water after preservation was measured by a method similar to that in Example 1. The measurement results of the number of nano-bubbles after preservation for 6 months are shown in Table 2, and the measurement results of the number of nano-bubbles after preservation for 12 months are shown in Table 3.

TABLE 2

| additive | number of nano-bubbles (bubbles/mL) |
| --- | --- |
| polysorbate 80 | $2.0 \times 10^8$ |
| poly(vinyl alcohol) | $7.0 \times 10^8$ |

TABLE 3

| additive | number of nano-bubbles (bubbles/mL) |
| --- | --- |
| polysorbate 80 | $2.3 \times 10^8$ |
| poly(vinyl alcohol) | $4.6 \times 10^8$ |

INDUSTRIAL APPLICABILITY

The nano-bubble water of the present invention comprising not less than $2.0 \times 10^8$ bubbles/mL of nano-bubbles shows a superior antibacterial action and can be preferably used as a base of a liquid pharmaceutical preparation such as injection and the like.

This application is based on patent application No. 2014-110209 filed in Japan, the contents of which are encompassed in full herein.

The invention claimed is:

1. A method of increasing the number of nano-bubbles in nano-bubble water to not less than $2.0 \times 10^8$ bubbles/mL, comprising forcedly dissolving a gas in the presence of a polyoxyethylene sorbitan fatty acid ester, poly(vinyl alcohol) and/or hydroxypropylcellulose in a pressurized container, flashing the gas into nano-bubble water through a nozzle, whereby the gas is supersaturated by depressurization and released as a mixture of micro-bubbles or nano-bubbles in the nano-bubble water, and allowing the micro-bubbles to naturally float and be released from the nano-bubble water, to increase the number of nano-bubbles in the nano-bubble water to not less than $2.0 \times 10^8$ bubbles/mL.

2. The method according to claim 1, wherein the nano-bubble water is produced in the presence of polysorbate 80 and/or poly(vinyl alcohol).

3. A method of maintaining the number of nano-bubbles in nano-bubble water at not less than $2.0 \times 10^8$ bubbles/mL, comprising forcedly dissolving a gas in the presence of a polyoxyethylene sorbitan fatty acid ester, poly(vinyl alcohol) and/or hydroxypropylcellulose in a pressurized container, flashing the gas into nano-bubble water through a nozzle, whereby the gas is supersaturated by depressurization and released as a mixture of micro-bubbles or nano-bubbles in the nano-bubble water, and allowing the micro-bubbles to naturally float and be released from the nano-bubble water, to maintain not less than $2.0 \times 10^8$ bubbles/mL in the nano-bubble water.

4. The method according to claim 3, wherein the nano-bubble water is produced in the presence of polysorbate 80 and/or poly(vinyl alcohol).

5. The method according to claim 4, wherein the number of nano-bubbles in the nano-bubble water is maintained at not less than $2.0 \times 10^8$ bubbles/mL for not less than 3 months.

6. A method of producing nano-bubble water comprising not less than $2.0 \times 10^8$ bubbles/mL of nanobubbles, comprising forcedly dissolving a gas in the presence of polysorbate 80 and/or poly(vinyl alcohol) in a pressurized container, flashing the gas into nano-bubble water through a nozzle, whereby the gas is supersaturated by depressurization and released as a mixture of micro-bubbles or nano-bubbles in the nano-bubble water, and allowing the micro-bubbles to naturally float and be released from the nano-bubble water, to produce the nano-bubble water comprising not less than $2.0 \times 10^8$ bubbles/mL of nanobubbles.

* * * * *